US00PP17367P3

(12) United States Plant Patent
Johansson

(10) Patent No.: US PP17,367 P3
(45) Date of Patent: Jan. 16, 2007

(54) **MAPLE TREE (*ACER TRUNCATUM*) VARIETY NAMED 'FIRE DRAGON'**

(50) Latin Name: *Acer truncatum*
Varietal Denomination: Fire Dragon

(76) Inventor: Keith G. Johansson, 6400 Saddle Ridge, Arlington, TX (US) 76016

( * ) Notice: Subject to any disclaimer, the term of this patent is extended or adjusted under 35 U.S.C. 154(b) by 0 days.

(21) Appl. No.: 11/104,027

(22) Filed: Apr. 12, 2005

(65) Prior Publication Data

US 2006/0230480 P1 Oct. 12, 2006

(51) Int. Cl.
*A01H 5/00* (2006.01)

(52) U.S. Cl. ..... Plt./224
(58) Field of Classification Search ..... Plt./224
See application file for complete search history.

(56) References Cited

U.S. PATENT DOCUMENTS

| | | | | |
|---|---|---|---|---|
| PP4,654 P | 2/1981 | Siebenthaler | ..... | Plt./51 |
| PP11,295 P | 3/2000 | Moon | ..... | Plt./221 |
| PP11,308 P | 3/2000 | Noack | ..... | Plt./101 |
| PP11,322 P | 4/2000 | Hanson | ..... | Plt./224 |

*Primary Examiner*—Kent Bell
*Assistant Examiner*—June Hwu
(74) *Attorney, Agent, or Firm*—Guy V. Manning

(57) ABSTRACT

A novel variety of the maple tree *Acer truncatum* was discovered in North Texas. It has a distinct lobular orbicular leaf shape, attributed to large lateral marginal lobes. It exhibits vibrant fall colors, including a distinctive cardinal or currant red and develops leaf margins tinged with Chinese yellow, giving the leaves the appearance of being afire. The variety known as 'Fire Dragon' also is hardy in extreme heat and wind conditions.

6 Drawing Sheets

Latin name of the genus and species and the variety denomination of the plant claimed: *Acer truncatum* 'Fire Dragon'.

BACKGROUND OF THE INVENTION

1. Field of the Invention

This invention relates generally to a new and distinct variety of decorative maple tree known generally by the scientific name *Acer truncatum.* I discovered it growing in a cultivated area in my nursery in Fort Worth, Tex., in 1999. I have given it the name 'Fire Dragon' because of its noticeable and distinctive spring, summer and particularly fall foliage.

No federally sponsored reasearch or development was involved in this invention.

2. Background

Maple trees provide desirable shade from spring to fall and typically shed their leaves for winter, thereby providing useful surrounding vegetation where summer sunlight may be excessive and winter sunshine is desirable. Displaying characteristically striking colors, maple trees are very ornamental and provide pleasing and varying visual effects throughout their foliage period.

The *Acer truncatum* maple tree, commonly called "Shantung" maple, is a newly introduced tree in the United States which does exceptionally well in the Midwest in hot climates and heavily alkaline soils. Shantung maples generally are characterized by having truncated base lobes near the leaf petiole and by having a prominent central lobe, giving the leaf a distinctly ovate-truncate shape. Fall foliage appears yellow, with occasional areas of lesser reds or orange mixed with yellow, though the latter seldom is repeated in subsequent years.

The instant novel variety of maple tree now discovered has substantially orbicular-lobular leaves, adapts well to wind and drought conditions, and consistently exhibits a fiery-red leaf, sometimes with yellow edges, giving the fall foliage a uniquely emblazoned appearance.

SUMMARY OF THE INVENTION

The novel cultivar of the present invention, named *Acer truncatum* 'Fire Dragon,' is believed to be a variant of *Acer truncatum* but distinguished by increased heat tolerance, a characteristic leaf shape and striking coloration variations. Specifically:

(a) its leaves have non-truncated base lobes and lobular margins, its side lobes being nearly as large as its central lobe, giving the leaf a distinctive orbicular profile;

(b) its fall colors exhibit a consistent, cardinal, occasionaly currant, red color with Chinese yellow tips and edges; and (c) it is very tolerant to high wind and drought conditions.

BRIEF DESCRIPTION OF THE DRAWINGS

FIG. 3 is a photographic close-up view of the major branches of the mature original tree of FIG. 1.

FIG. 4A is a photographic close-up of one of the summer color variations (rose madder) of the mature original tree of FIG. 1.

FIG. 4B is a photographic view of a plurality of young, grafted Fire Dragon trees exhibiting late spring growth characteristics of the mature original tree of FIG. 1.

FIG. 5A is a photographic close-up of another of the summer color variations (garnet brown) of the mature original tree of FIG. 1.

FIG. 5B is a photographic close up of a new spring growth color variation (burnt orange) of the mature original tree of FIG. 1.

FIG. 6 is a photographic view of summer foliage on hardened branches from the mature original tree of FIG. 1.

FIGS. 9A and 9B are distant and close-up, respectively, photographic views of a branch of the mature original tree of FIG. 1 exhibiting leaves having a distinctive currant red coloration with fiery (Chinese yellow) margins.

FIG. 10 depicts an example of the newly discovered variety of maple tree in winter, defoliated and with snow cover enhancing its branch structure.

FIG. 11 depicts the mature original tree of FIG. 1 in winter time without foliage, showing branch structure.

FIG. 12 depicts an example branch showing bud patterns of the mature original tree of FIG. 1.

DETAILED DESCRIPTION OF THE INVENTION

The instant variety of maple tree was discovered as a seedling growing among other maple trees of the *Acer truncatum* species at my nursery in Fort Worth, Tex., in 1999. It was successfully asexually reproduced at said nursery by grafting onto *Acer truncatum* seedlings and by semi-hardwoood cuttings. The novel characteristics are reliably transmitted to succeeding generations.

With reference to the six (6 y.o.) year old tree depicted in the figures, the following specific description of the instant maple variety details its unique characteristics. Color terminology refers to The 1941 Royal Horticultural Society (R.H.S.) Colour Chart.

Origin: A tree of unknown origin, Fire Dragon is similar to other *Acer truncatum* varieties except for spring, summer and fall leaf coloration, leaf shape and a notable tolerance for wind and drought conditions. In particular, the spring leaf coloration exhibits burnt orange (RHS 014/3) overtones rather than the normal reddish-purple (RHS dahlia purple 931/3) overtones of typical *Acer truncatum.* Summer leaf coloration during hot weather prevalent in Texas exhibits the spring coloration, a rose madder (RHS 23/3) or a darker tone of garnet brown (RHS 918/3), as opposed to the aforementioned reddish purple. Fall coloration is a most unique and consistent exhibit of cardinal red (RHS 822/3), whereas other *Acer truncatum* leaves are mostly yellow, with only occasional areas of lesser red or orange mixed with yellow, and seldom repeated in subsequent years. Leaf shape matches the *Acer truncatum* profile by only approximately one (1%) percent, differing mostly by (a) not having truncated leaf bases and (b) having lobular margins with side lobes nearly as large as the central lobe (*Acer truncatum* has a prominent central lobe, creating an ovate-truncate shape), giving the leaf a substantially orbicular shape.

Classification: *Acer truncatum* 'Fire Dragon'.

Parentage: Unknown; believed to be a seedling variation, mutation or adaptation of *Acer truncatum.*

Figure 1:
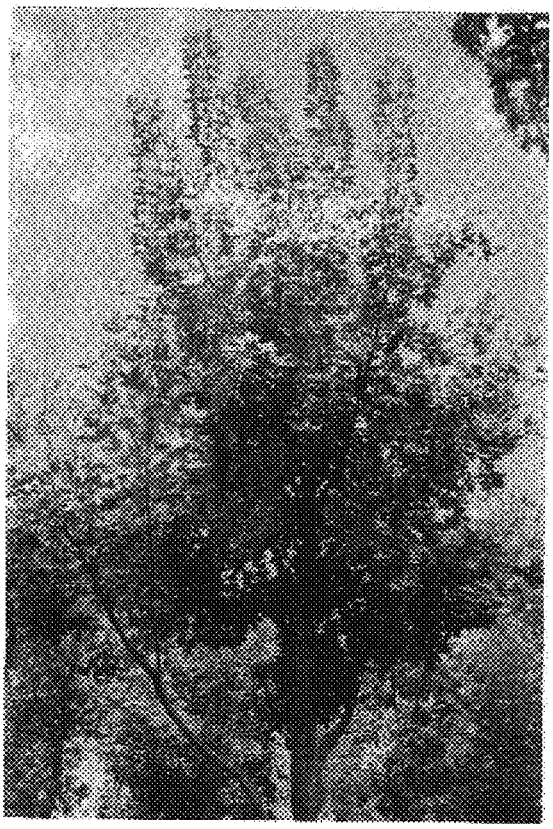
FIG. 1 is a photographic view of a mature original tree in summer.

Shape: Deciduous tree with rounded crown and many vigorous, crowded stems. See FIG. 1. Caliper size is two and one-half (2½) inches in four (4) years, measured eighteen (18") inches up from ground level.

Height: Five to six (5–6 ) meters, increasing an average of one to one and one-half (1–1.5 m/yr) meters per year, slowing with age but expected to reach twelve to fifteen, and occasionally eighteen (12–15, 18 m) meters at maturity, as typical of *Acer truncatum.* See FIG. 1.

Spread: Four (4 m), meters, increasing an average of one half to one (0.5–1.0 m/yr) meters per year, slowing with age but expected to reach ten to fourteen, and occasionally sixteen (10–14, 16 m) meters at maturity, as typical of *Acer truncatum.* See FIG. 1.

Figure 2:
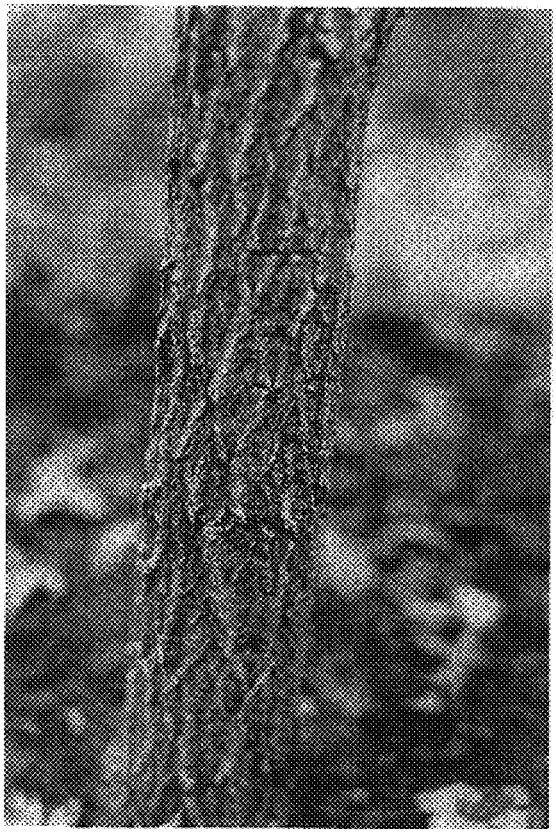
FIG. 2 is a photographic view of the trunk mature original tree of FIG. 1.
Figure 7:
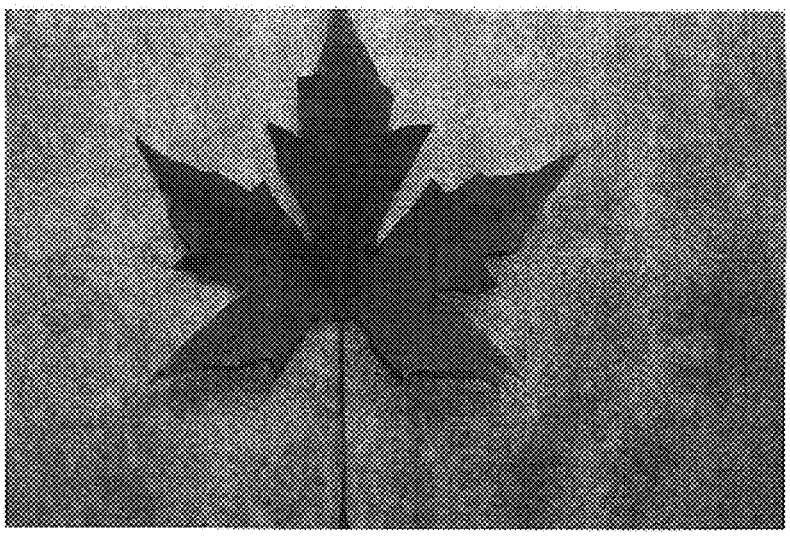
FIG. 7 is a photographic view of a single leaf of the mature original tree of FIG. 1 exhibiting the cardinal red fall coloration.
Figure 8:
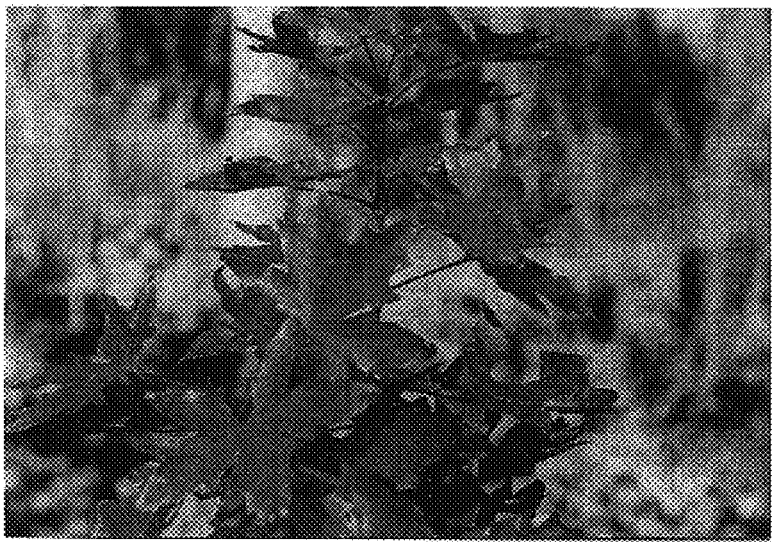
FIG. 8 is a photographic close-up view of a branch of the mature original tree of FIG. 1 exhibiting the cardinal red fall coloration.
Figure 9A:
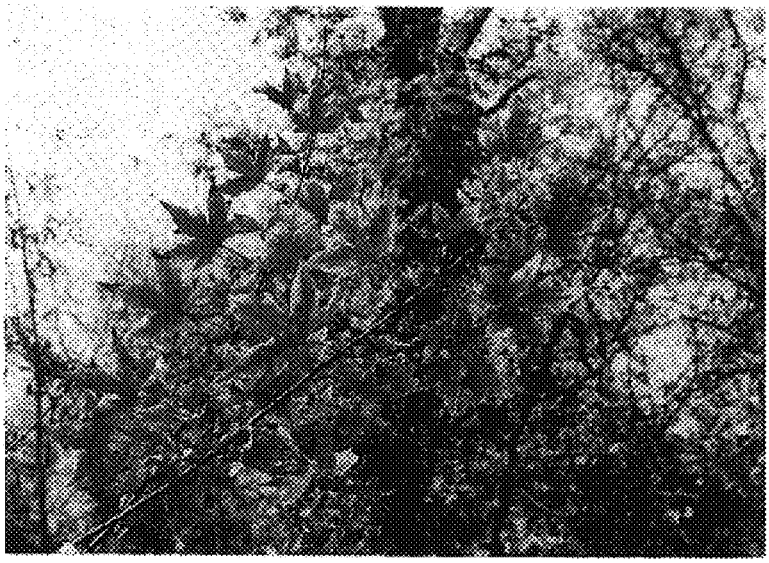

Trunk: Heavily fissured bark with light brown raised areas and dark brown recessed areas. See FIG. 2. Size increases approximately two 2 cm.) centimeters per growing season.

Branches: Current year wood is light gray to brown, glaucous. Develops purplish-brown overtones in winter. Third year wood is very hard and dense. Lenticels are sparse, straw-colored and oval. See FIG. 3.

Leaves:

*Shape.*—Five (5) lobes, somewhat wavy and leathery, five to eleven, averaging seven, (5–11, 7 cm.) centimeters in length, usually two (2 cm) less across. Glabrous, with ovate lobes, lobular margins, acuminate apices, cordate bases and tufted, veined axils on the underside. See FIGS. 4A–9.

*Color.*—The spring leaf coloration has burnt orange (RHS 014/3) (FIG. 5B) overtones. Summer leaf coloration of new growth during hot weather prevalent in Texas exhibits the spring burnt orange (RHS 014/3) (FIG. 5B), rose madder (RHS 23/3) (FIG. 4A) or a darker tone of garnet brown (RHS 918/3) (FIG. 5A). Hardened growth foliage has a shiny spinach green (RHS 960) on the leaf top with a slightly lighter tint on the bottom (RHS 960/2) under good fertilization. See FIG. 6. Fall coloration is cardinal red (RHS 822/3) (FIGS. 7 and 8), and during a long, hot fall, a currant red (RHS 821/3), usually developing a striking Chinese yellow (RHS 606/1) around the tips and edges. See FIGS. 9A and 9B.

Petiole: Slender, fern green (RHS 862/3) in summer, from four to thirteen (average 8) 4–13 cm.) in length, glabrous. Red in the fall (same color as the leaf). See FIG. 7. Milky sap produced when broken.

Winter buds: Terminal buds two to four (2–4 mm.) millimeters in length, one to two 1–2 mm) in diameter, ovoid, brown in color. Lateral buds generally similar but smaller See FIG. 12.

Flowering: Flowering season is spring (early April in Texas), before or simultaneously with leaves on terminal, forty by forty to sixty (40×40–60 mm) millimeter corymbose racemes having unequal, ten to twenty (10–20 mm.) millimeter length stems. Each 5-merous bloom is deep saucer-shaped, ten (10 mm) millimeters long and eight (8 mm) deep, with oblong to ovate petals and supported on one (1 cm) centimeter pedicels. Straw yellow (RHS 604/1) color.

Reproductive organs: Imperfect; monoecious; trees first produce blooms of one gender, then of the other, then of the first again, often having both at the same time; approximately half of trees begin with each gender. Blooms have a central, circular, slightly lobed, straw yellow (RHS 604/1) pistil with an ovary supported on two divergent stigma arms with short, one (1 mm) styles. Pistil is surrounded by eight to ten (8–10) one (1 mm) millimeter, glabrous stamens with numerous oval, two (2 mm) millimeter anthers on five to six (5–6 mm) millimeter filaments. In the male flowers, filaments are longer, sometimes extending the anthers above the perianth, with a diminished pistil and vestigial ovary. Female blooms have shorter filaments wherein the smaller anthers are almost concealed within the perianth.

Pollen: Same color as flowers (straw yellow— RHS 604/1).

Fruit: None observed; expected to be very similar to other *Acer truncatum* varieties, having pendulous, yellow-to-reddish, wide-angled samaras, three (3 cm) centimeters long by one (1 cm) centimeter wide, with ovoid or obovoid, smooth and flattened nutlets one and one-half (1.5 cm) centimeters long, one (1 cm) broad and two to three (2–3 cm) centimeters thick, ripening in the fall (October in Texas).

Disease resistance: No known problems.

Climate: Adapts well to any well-drained soil, even highly alkaline, clay soils. Very drought tolerant, wind tolerant and hardy to Zone 4 (USDA hardness guidelines). More drought tolerant than other *Acer truncatum* varieties, it exhibits a good ability to keep healthy new growth without wilting under extreme heat conditions.

Comparison to other *Acer truncatum* varieties:

*Crown.*—Similar rounded crown and expected height and spread.

*Trunk.*—Similar heavily fissured trunk, with light brown raised areas between dark brown fissures.

*Flowers.*—Similar straw-yellow, identical in size.

*Reproductive organs.*—Similar monoecious imperfect, pollen same color as blooms.

*Fruit.*—Expected to be similar or identical.

*Fall color.*—Distinctive cardinal red (RHS 822/3) and, during a long, hot fall, a currant red (RHS 821/3) with Chinese yellow (RHS 606/1) around the tips and edges, rather than the normal yellow to orange with occasional red areas of typical *Acer truncatum.*

*Leaf shape and size.*—Only slightly polymorphic, the Fire Dragon maple has very few truncated leaf bases and has lobulate margins with side lobes nearly as large as the central lobe (versus *Acer truncatum's* prominent central lobe and noticeably greater tendency toward the polymorphic), giving the leaf a substantially orbicular shape. Size is similar or slightly smaller. Overall effect is to give the tree a cleaner look when compared to other varieties.

*Hardiness.*—Even more heat and drought tolerant. Where most *Acer truncatum* varieties survive reliably in the extreme climate conditions, alkaline soils and urban pollution conditions of North Texas, Fire Dragon seems to thrive in said conditions, keeping healthy new growth without wilting even in extreme heat conditions, yet tolerant of ice and wind storms.

I claim:

1. A new and distinct variety of an *Acer truncatum* maple tree named "Fire Dragon", as described and illustrated herein.

* * * * *

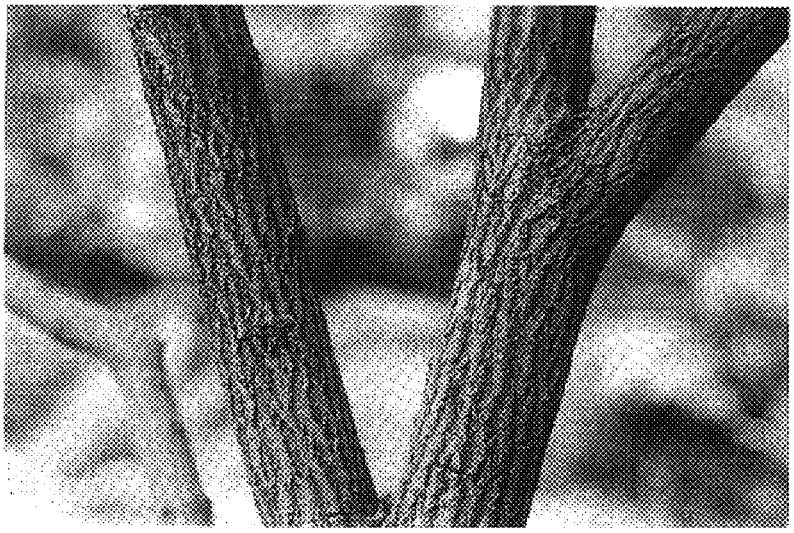
Fig. 3
Fig. 4A
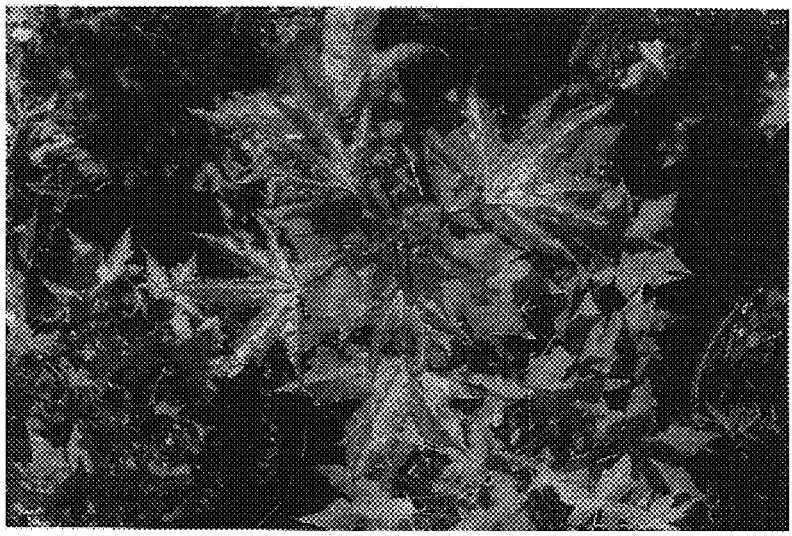
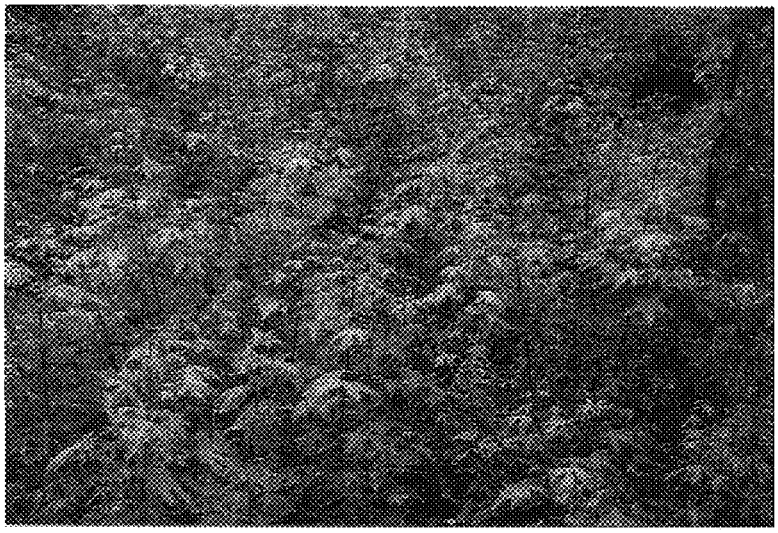
Fig. 4B

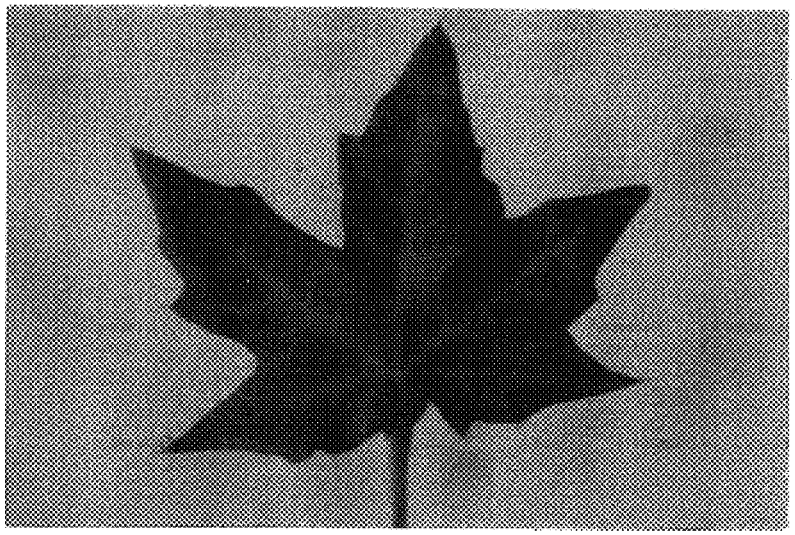
Fig. 5A
Fig. 5B
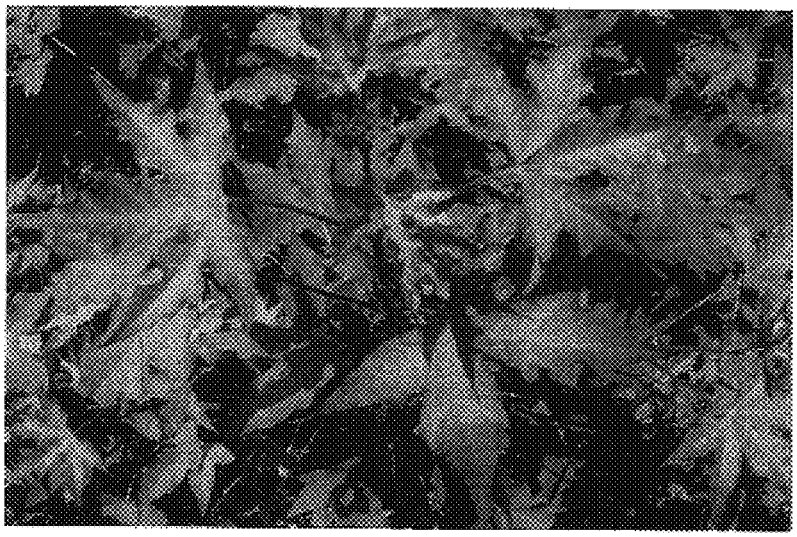
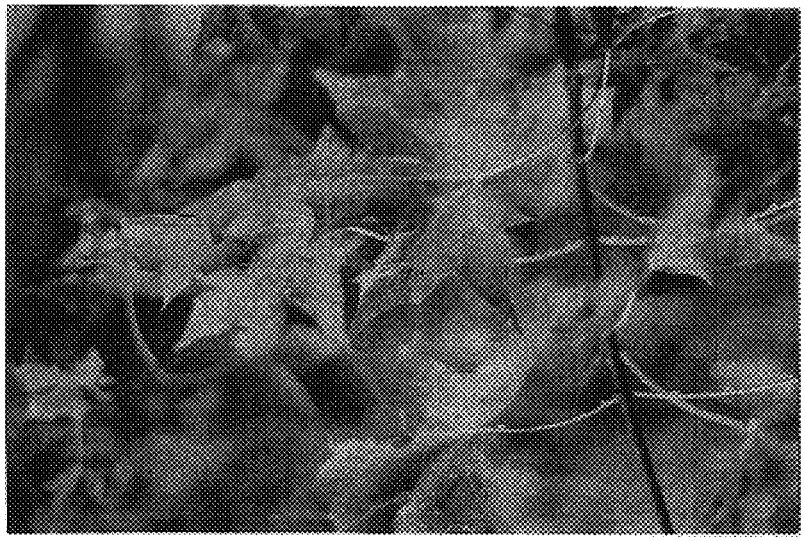
Fig. 6

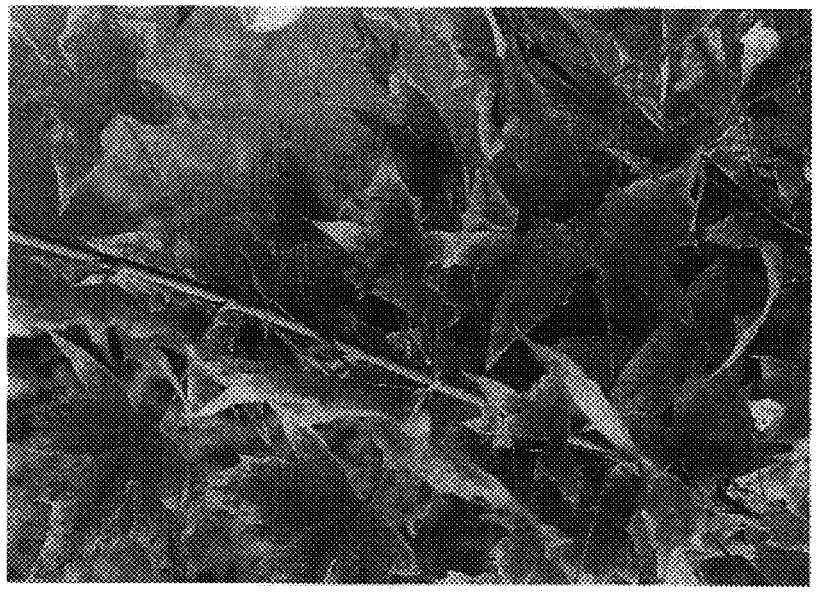
Fig. 9B
Fig. 10
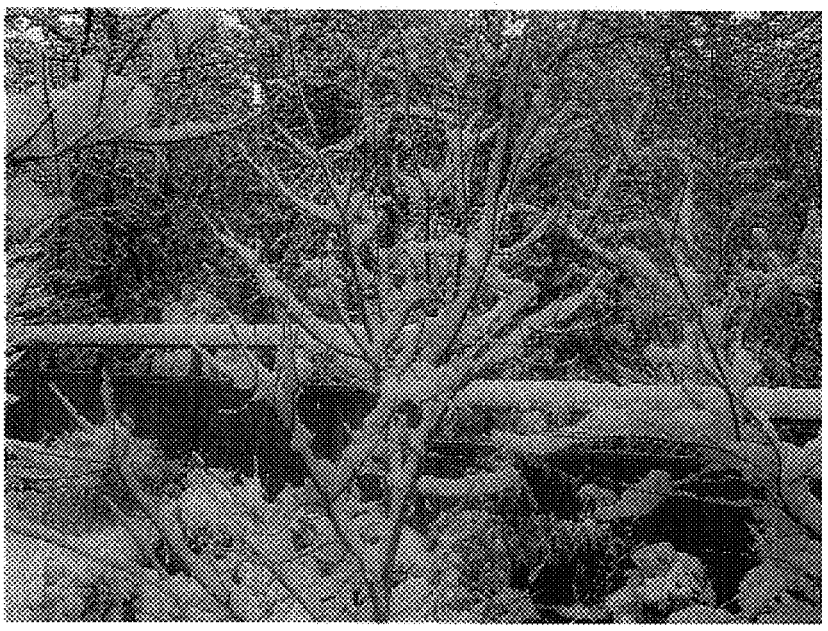

Fig. 11
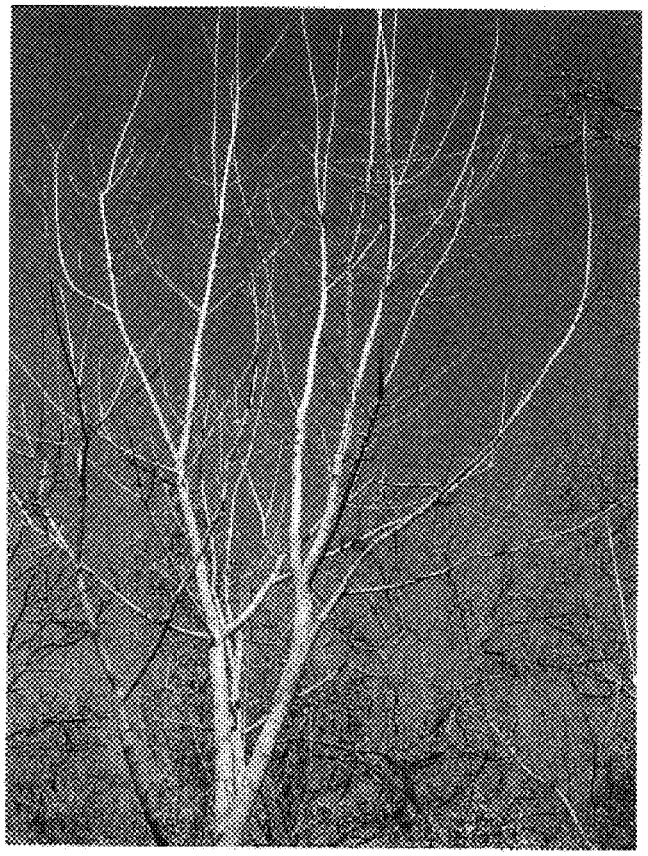
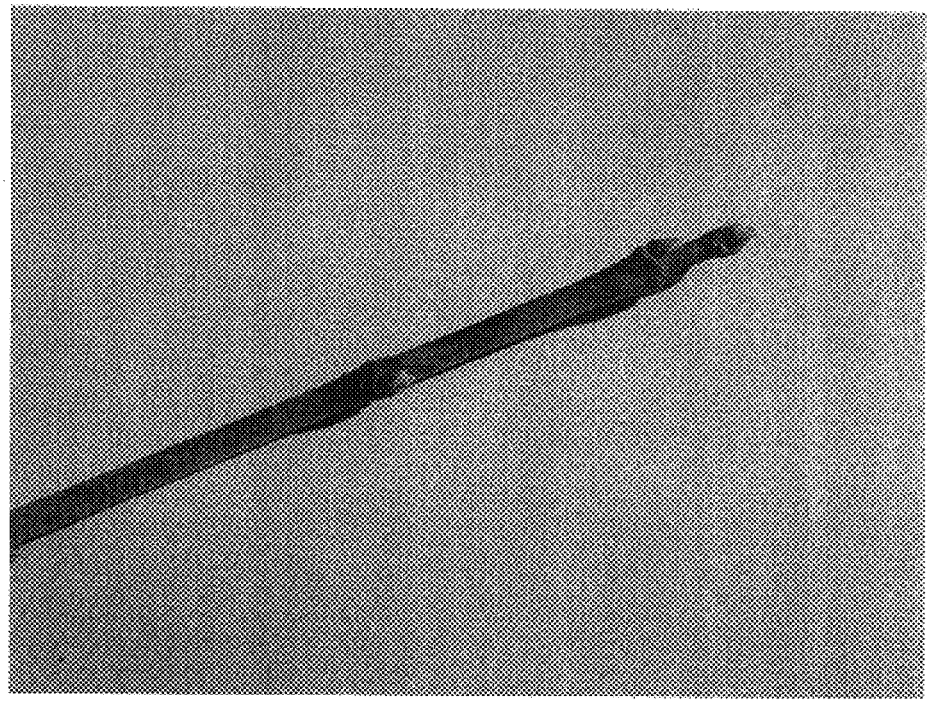
Fig. 12